United States Patent
Razzano

[11] Patent Number: 6,037,486
[45] Date of Patent: Mar. 14, 2000

[54] CRACKING OF FLUOROSILICONES TO PRODUCE 1,3, 5-TRIS (3,3,3-TRIFLUOROPROPYL)-1,3,5-TRIMETHYLCYCLOTRISILOXANE

[75] Inventor: John S. Razzano, Cohoes, N.Y.

[73] Assignee: General Electric Company, Pittsfield, Mass.

[21] Appl. No.: 09/207,568

[22] Filed: Dec. 8, 1998

Related U.S. Application Data

[60] Provisional application No. 60/067,727, Dec. 8, 1997.

[51] Int. Cl.[7] .................................................. C07F 7/08
[52] U.S. Cl. ................................................... 556/460
[58] Field of Search ............................................ 556/460

[56] References Cited

U.S. PATENT DOCUMENTS

| | | | |
|---|---|---|---|
| 2,816,124 | 12/1957 | York | 556/460 |
| 3,110,720 | 11/1963 | Pike | 556/460 |
| 3,846,464 | 11/1974 | Razzano . | |
| 4,111,973 | 9/1978 | Bluestein . | |
| 4,689,420 | 8/1987 | Baile et al. | 556/460 |
| 5,241,097 | 8/1993 | Zupancic et al. . | |
| 5,247,116 | 9/1993 | Buese et al. | 556/460 |
| 5,420,325 | 5/1995 | Razzano . | |
| 5,491,249 | 2/1996 | Kostas . | |
| 5,545,837 | 8/1996 | Kobayashi | 556/460 |
| 5,670,689 | 9/1997 | Allandrieu et al. | 556/460 |

*Primary Examiner*—Paul F. Shaver

[57] ABSTRACT

The present invention relates to an improved cracking process for increasing the yield and purity of fluoro-alkyl substituted cyclic compounds by using an alkali metal carbonate for the cracking catalyst.

17 Claims, No Drawings

CRACKING OF FLUOROSILICONES TO PRODUCE 1,3, 5-TRIS (3,3,3-TRIFLUOROPROPYL)-1,3,5-TRIMETHYLCYCLOTRISILOXANE

This application claims rights of priority from U.S. Provisional Patent Application Ser. No. 60/067,727, filed Dec. 8, 1997, which is hereby incorporated by reference.

FIELD OF THE INVENTION

The present invention relates to an improved method of making cyclic siloxanes. It is concerned with fluorohydrolyzates that incorporate the use of alkali metal carbonates for cracking to produce fluoro-alkyl substituted cyclic siloxane compounds.

BACKGROUND OF THE INVENTION

Polymer used to make fluorosilicone rubber is made by the specialized ring opening polymerization of 1,3,5-tris(3, 3,3-trifluoropropyl)-1,3,5-trimethylcyclotrisiloxane, hereinafter fluoro cyclic trimer. Fluoro cyclic trimer is commercially produced in a cracking process where methyltrifluoropropylsiloxanes are heated to temperatures in excess of 200° C. in the presence of a rearrangement catalyst and the relatively lower boiling cyclic trimer is fractionally distilled from the reactor at high purity. The process produces fluorosilicone cyclic trimer at a slow rate that requires long contact times between the siloxane mass and the strong base typically used as a cracking catalyst. These conditions of cracking cause side reactions between the siloxane mass and the catalyst.

The cracking process can be operated as either a one step process where pure fluoro cyclic trimer is taken from the top of a fractionating column attached to the reactor, or a two step process, i.e., cracking with a small fractionating column or no fractionating column to produce crude fluoro cyclic trimer overhead followed by a standard distillation to produce high purity fluoro cyclic trimer.

Processes using cracking catalysts to produce cyclic trimer are well known in the art. Catalysts which have traditionally been used in the art are alkali metal compounds, preferably alkali metal hydroxides, including potassium hydroxide (KOH) and sodium hydroxide (NaOH) with octadecanol. Undesirable side reactions that occur under the conditions that produce cyclic trimer using these traditional catalysts include: dehydrohalogenation of the trifluoropropyl groups which produces unsaturated siloxanes; and cleavage of the trifluoropropyl group creating a trifunctional group which reduces yield of the desired cyclic trimer. The NaOH in octadecanol catalyst system causes less of these side reactions than the KOH, but the level of side reactions using NaOH in octadecanol is still undesirable. Additionally, because of the presence of these side reactions, the maximum temperature at which the reaction can be efficiently operated is limited to about 225° C. Further, alkali metal hydroxides cause the dehydrofluorination reaction and the cleavage reaction resulting in the deactivation of the active catalyst which reduces both the reaction rate and the length of the run.

SUMMARY OF THE INVENTION

There is provided in accordance with the present invention a process for improving the yield and purity of fluoro-alkyl substituted cyclic siloxanes comprising: (a) adding to a silicone fluorohydrolyzate, an effective amount of a metal alkali carbonate cracking catalyst; and (b) reacting said fluorohydrolyzate in the presence of said carbonate cracking catalyst to produce the fluoro-alkyl substituted cyclic siloxane compounds.

Examples of alkali metals that may be used in the carbonate catalyst include: potassium, cesium and rubidium.

The invention additionally provides for recovering the fluoro cyclic trimer. The recovered cyclic trimer can be very high purity in a one step process, or can be lower purity to be purified in a separate distillation step.

There is also provided in accordance with the present invention a lower level of undesirable side reactions including: decreasing the extent of the undesirable dehydrofluorination reaction, and decreasing the undesirable cleavage reaction.

There is also provided with this invention the ability to raise the reactor temperature above 220–225° C., the maximum normally achievable using KOH or NaOH catalysts.

DETAILED DESCRIPTION OF THE INVENTION

The present invention is directed to the production of fluoro-alkyl substituted cyclic siloxanes such as 1,3,5-tris(3, 3,3-trifluoropropyl)-1,3,5-trimethylcyclotrisiloxane and higher molecular weight methylperfluoroalkylethyleneyl based cyclic siloxane trimers and related cyclic compounds by using alkali metal carbonates as a catalysts for the cracking reaction.

As used herein, the term "fluoro-alkyl" is defined as a monovalent straight or branched alkyl group having 3 or more carbon atoms, preferably 3 to 8 carbon atoms, with all carbon atoms from the third to the $n^{th}$ fully substituted with fluorine, such as, for example, fluoropropyl and fluorobutyl.

As used herein, the term "fluorohydrolyzate" has the empirical formula:

$$R(R^3CH_2CH_2)SiO$$

where R is alkyl, preferably $C_1$ to $C_6$, most preferably methyl, and $R^3$ is a perfluoroalkyl group.

The key feature of this invention is the addition of an effective amount of an alkali metal carbonate catalyst. The alkali metal carbonate is preferably selected from the class consisting of: Potassium carbonate, Cesium carbonate and Rubidium carbonate, more preferably from the group consisting of Potassium carbonate and Cesium carbonate. The most preferred catalyst is Potassium carbonate.

In a typical example, potassium carbonate is added to a siloxane cracking reactor in a desired range of from about 0.01 to about 10 weight percent of the fluorohydrolyzate, more preferably in a range of from about 0.1 to about 5 weight percent, and most preferably in a range of from about 0.25 to about 2.5 weight percent. In the initial example, potassium carbonate was added to the reactor at 2 weight percent of the charge. The potassium carbonate is insoluble in the siloxane phase and the reaction is thought to take place on the solid surfaces of the potassium carbonate. The reaction is thus an interfacial cracking reaction. Because the potassium carbonate catalyst is a solid, the catalyst lasts for a very long time allowing essentially semi-continuous runs of long duration.

In the prior art process, the use of catalysts, such as alkali metal hydroxide catalysts, increased the level of undesirable side reactions. Some examples that relate to means of practicing the present invention known to those having ordinary skills in the art are discussed below. U.S. Pat. No.

4,111,973 to Bluestein discloses a process for preparing fluoroalkyl cyclotrisiloxanes using alkali metal hydroxide catalysts and an effective amount of a higher aliphatic alcohol as a stabilizing agent. In the case of fluoroalkyl siloxanes, the alcohol was added to activate the catalyst. U.S. Pat. No. 5,420,325 to Razzano discloses a process in which siloxane hydrolyzates containing high trifunctional units can be continuously cracked in the liquid phase without forming a gel by adding an effective amount of high boiling alcohol to prevent gelation. U.S. Pat. No. 3,846,464 to Razzano discloses a process for producing cyclic methylvinylsiloxanes using a potassium hydroxide catalyst and a high boiling hydrocarbon solvent. U.S. Pat. No. 5,491,249 to Kostas discloses a process for producing cyclic polysiloxanes using acid catalysts. U.S. Pat. No. 5,241,097 to Zupancic et al. discloses a process for producing cyclic siloxanes in a biphasic reaction solvent mixture comprising an alkane, an alcohol and water.

Unexpectedly, the use of the alkali metal carbonate catalyst results in lower levels of the undesirable side reactions, producing about a 50% decrease in the extent of the undesirable dehydrofluorination reaction, about a 50% decrease in the undesirable cleavage reaction and minimizing deactivation of the catalyst.

In none of the prior art references, supra, is there any suggestion or demonstration in which an alkali metal carbonate catalyst is used. The present invention is based on the discovery that an alkali metal carbonate used as a catalyst, wherein the fluorohydrolyzate contains a trifluoropropyl group, will produce fluoro-alkyl substituted cyclic siloxanes such as 1,3,5-tris(3,3,3-trifluoropropyl)-1,3,5-trimethylcyclotrisiloxane, 1,3,5-tris(perfluoroalkyl-ethyleneyl)-1,3,5-trimethylcyclotrisiloxane, and other related cyclic compounds.

The present invention thus provides a means to produce 1,3,5-tris(3,3,3-trifluoropropyl)-1,3,5-trimethylcyclotrisiloxane and related cyclic compounds while decreasing the level of undesirable side reactions, decreasing the extent of the undesirable dehydrofluorination reaction, decreasing the undesirable cleavage reaction and minimizing deactivation of the catalyst.

The production of fluoro cyclic trimer is a function of the reactor temperature and the distillation rate of the fluoro cyclic trimer out of the reactor. Any known distillation techniques may be used to separate the cyclic siloxanes formed in the cracking reaction. The quantity of fluoro cyclic trimer present in the reactor absent any other considerations is primarily a function of the maximum equilibrium amount of fluoro cyclic trimer allowed by thermodynamic equilibrium which may be shifted in the approach to equilibrium by the law of mass action by means of distilling the desired reaction product, the fluoro cyclic trimer, out of the reactor.

Because the amount of fluoro cyclic trimer does in fact increase with reaction temperature, if the reaction temperature can be increased, the amount of fluoro cyclic trimer produced per unit time can be increased. The maximum temperature allowable when NaOH in octadecanol is used as a catalyst is about 220° C. because of the presence of undesirable side reactions which reduce the yield of the desired product. Because fewer side reactions occur using an alkali metal carbonate catalyst at a temperature of 220° C., the reactor temperature can be increased to higher temperatures ranging from about 240° C. to about 250° C. without increasing the rate of undesirable side reactions to unacceptable levels. The desired temperature range maintained during the reaction is from about 120° C. to about 275° C., with a preferred range of 150° C. to about 260° C. The desired pressure range is from about 5 mm Hg to about 100 mm Hg, with a preferred range from about 20 mm Hg to about 80 mm Hg, with a most preferred range of from about 35 mm Hg to 50 mm Hg. The desired reflux ratio is from about 1:5 to about 15:1, with a preferred reflux ratio of from about 1:5 to about 10:1. The reflux ratio is much lower for a two step process; for a one step process it will typically be about 10:1.

In order that those skilled in the art might better be able to practice the present invention, the following examples are given by way of illustration and not by way of limitation. The examples are not given for any purpose of setting limits or defining the scope of the instant invention.

All United States patents referenced herein are herewith and hereby specifically incorporated by reference.

Experimental

A typical experiment uses between 250 and 300 grams of fluorohydrolyzate, linear polymeric methyltrifluoropropylsiloxanes, in a reactor with an attached distillation column having 4–5 theoretical plates and a reflux splitter. The cracking runs were conducted at 220° C. to 240° C. and a vacuum of from about 35 to about 50 mm Hg. When measurement of the trimer production rate was technically appropriate, a high take-off rate with a reflux ratio of 1:5 was used. For a one step process, a higher reflux ratio is generally used, typically in the range of 10:1 to 12:1. This high rate produced a mixture of fluoro cyclic trimer, fluoro cyclic tetramer and fluoro cyclic pentamer. The trimer content of this mixture is measured and the trimer production rate is calculated from the trimer content and the total take-off.

EXAMPLE 1

The catalyst used was 1 percent by weight of 50 weight percent aqueous NaOH and 1 percent by weight stearyl (octadecanol) alcohol. Take-off was begun when reaction conditions were reached. The production rate of fluoro cyclic trimer was 2.4 and 2.7 grams per minute in two separate experiments.

EXAMPLE 2

This is a repeat of example 1 except that the charge was pre-reacted for 35 hours with no take-off. Take-off was begun at 230° C. at a reflux ratio of 1:5. The production rate of fluoro cyclic trimer was 1.36 grams per minute.

EXAMPLE 3

Potassium carbonate ($K_2CO_3$) was added as 2 weight percent of the charge weight. Take-off was begun when reaction conditions were reached. The production rate of fluoro cyclic trimer was 2.6 grams per minute.

EXAMPLE 4

These were a duplication of example 3 except that the charges were pre-reacted for 35 hours at 220° C. with no take-off. Take-off was begun at 220° C. to 230° C. at a reflux ratio of 1:5. The production rate of fluoro cyclic trimer in the two separate experiments was 2.85 and 2.97 grams per minute.

Results of these experiments are summarized in Table 1.

TABLE 1

(summarized results of Experiments 1 to 4)

| No. | Catalyst Type | Amount of Catalyst | Take-off (when started) | Reflux Ratio | Prod. Rate Trimer (gm/min) |
|---|---|---|---|---|---|
| 1 | NaOH and octadecanol alcohol | 1% by wt | When reaction reached reaction conditions | 1:5 | 2.4 |
| 1 | NaOH and octadecanol alcohol | 1% by wt | When reaction reached reaction conditions | 1:5 | 2.7 |
| 2 | NaOH and octadecanol alcohol | 1% by wt | Pre-react 35 hours, take off at 230° C. | 1:5 | 1.36 |
| 3 | $K_2CO_3$ | 2% by wt | When reaction reached reaction conditions | 1:5 | 2.6 |
| 4 | $K_2CO_3$ | 2% by wt | Pre-react 35 hours, take off at 220–230° C. | 1:5 | 2.85 |
| 4 | $K_2CO_3$ | 2% by wt | Pre-react 35 hours, take off at 220–230° C. | 1:5 | 2.97 |

From Table 1, it can be seen that the potassium carbonate ($K_2CO_3$) catalyst deactivates much more slowly than the standard NaOH catalyst system and that the production rate of fluoro cyclic trimer is greater with the $K_2CO_3$ catalyst.

Having described the invention that which is claimed is:

1. A process for improving the yield and purity of fluoro-alkyl substituted cyclic siloxane compounds, comprising:
   (a) adding to a silicone fluorohydrolyzate, an effective amount of an alkali metal carbonate cracking catalyst; and
   (b) reacting said fluorohydrolyzate in the presence of said catalyst to produce the fluoro-alkyl substituted cyclic siloxane compounds, wherein the heating temperature varies from about 120° C. to about 275° C., the vacuum varies from about 5 to about 100 mm Hg, and the reflux ratios from about 1:5 to 15:1.

2. The process of claim 1, wherein the silicone fluorohydrolyzate contains a trifluoropropyl group.

3. The process of claim 1, wherein the silicone fluorohydrolyzate has the empirical formula $R(R^3CH_2CH_2)SiO$ where R is alkyl, preferably $C_1$ to $C_6$, most preferably methyl, and $R^3$ is perfluoroalkyl group.

4. The process of claim 2, wherein the silicone fluorohydrolyzate is methyltrifluoropropylsiloxane.

5. The process of claim 1, wherein the catalyst is selected from the group consisting of: Potassium carbonate, Cesium carbonate and Rubidium carbonate.

6. The process of claim 5, wherein the catalyst is selected from the group consisting of: Potassium carbonate and Cesium carbonate.

7. The process of claim 5, wherein the catalyst is Potassium carbonate.

8. The process of claim 5, wherein the catalyst is present at a concentration of from about 0.01 to about 10% by weight of the fluorohydrolyzate siloxane composition.

9. The process of claim 8, wherein the catalyst is present at a concentration of from about 0.1 to about 5% by weight of the fluorohydrolyzate siloxane composition.

10. The process of claim 9, wherein the catalyst is present at a concentration of from about 0.25 to about 2.5% by weight of the fluorohydrolyzate siloxane composition.

11. The process of claim 1, wherein the heating temperature varies from about 150° C. to about 260° C.

12. The process of claim 1, wherein the vacuum varies from about 20 to about 80 mm Hg.

13. The process of claim 12, wherein the vacuum varies from about 35 to about 50 mm Hg.

14. The process of claim 1, wherein the reflux ratio is from about 1:5 to 10:1.

15. The process of claim 1, wherein the fluoro-alkyl substituted cyclic siloxane compound is 1,3,5-tris(3,3,3-trifluoropropyl)-1,3,5-trimethylcyclotrisiloxane.

16. The process of claim 1, wherein the fluoro-alkyl substituted cyclic siloxane compound is 1,3,5-tris (perfluoroalkyl-ethyleneyl)-1,3,5-trimethylcyclotrisiloxane.

17. The process of claim 1, wherein the fluoro-alkyl substituted cyclic siloxane trimer compounds are recovered by distillation.

* * * * *